(12) United States Patent
Wang et al.

(10) Patent No.: US 6,475,184 B1
(45) Date of Patent: Nov. 5, 2002

(54) CATHETER SHAFT

(75) Inventors: Yiqun Bruce Wang, Maple Grove, MN (US); Lixiao Wang, Long Lake, MN (US); Daniel J. Horn, Shoreview, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 157 days.

(21) Appl. No.: 09/593,193

(22) Filed: Jun. 14, 2000

(51) Int. Cl.$^7$ .............................................. A61M 11/00
(52) U.S. Cl. ................. 604/93.01; 604/167.06
(58) Field of Search .................. 604/96.01, 167.06, 604/160, 264; 606/41, 28

(56) References Cited

U.S. PATENT DOCUMENTS

| | | | |
|---|---|---|---|
| 4,748,982 A | 6/1988 | Horzewski et al. ......... 128/344 |
| 4,762,129 A | 8/1988 | Bonzel ........................ 128/344 |
| 4,771,777 A | 9/1988 | Horzewski et al. ......... 128/344 |
| 4,846,174 A | 7/1989 | Willard et al. ............... 128/344 |
| 4,846,791 A | 7/1989 | Hattler et al. ................. 604/43 |
| 4,867,174 A | 9/1989 | Skribiski .................... 128/772 |
| 4,917,103 A | 4/1990 | Gambale et al. ............ 128/772 |
| 4,922,923 A | 5/1990 | Gambale et al. ............ 128/772 |
| 4,960,410 A | 10/1990 | Pinchuk ........................ 604/96 |
| 4,988,356 A | 1/1991 | Crittenden et al. ......... 606/192 |
| 4,762,129 A | 7/1991 | Bonzel ........................ 606/194 |
| 5,040,548 A | 8/1991 | Yock .......................... 128/898 |
| 5,061,273 A | 10/1991 | Yock .......................... 606/194 |
| 5,154,725 A | 10/1992 | Leopold ...................... 606/194 |
| 5,156,594 A | 10/1992 | Keith ............................ 604/96 |
| 5,180,367 A | 1/1993 | Kontos et al. .............. 604/101 |
| 5,180,376 A | 1/1993 | Fischell ...................... 604/282 |
| 5,217,482 A | 6/1993 | Keith .......................... 606/194 |
| 5,232,445 A | 8/1993 | Bonzel ........................ 604/96 |
| 5,252,159 A | 10/1993 | Arney ......................... 156/169 |
| 5,279,562 A | 1/1994 | Sirhan et al. ................. 604/96 |
| 5,300,025 A | 4/1994 | Wantink ..................... 604/191 |
| 5,300,085 A | 4/1994 | Yock .......................... 606/191 |
| 5,306,247 A | 4/1994 | Pfenninger ................... 604/96 |
| 5,316,016 A | 5/1994 | Adams et al. ............... 128/774 |
| 5,324,269 A | * 6/1994 | Miraki ........................ 604/160 |
| 5,334,147 A | 8/1994 | Johnson ........................ 604/96 |
| 5,338,295 A | 8/1994 | Cornelius ..................... 604/96 |
| 5,350,395 A | 9/1994 | Yock .......................... 606/194 |
| 5,364,376 A | 11/1994 | Horzewski et al. ......... 604/280 |
| 5,370,616 A | 12/1994 | Keith et al. ................. 604/102 |
| 5,380,283 A | 1/1995 | Johnson ........................ 604/96 |
| 5,387,193 A | 2/1995 | Miraki ........................ 604/96 |
| 5,389,087 A | 2/1995 | Miraki ........................ 604/247 |
| 5,395,334 A | 3/1995 | Keith et al. ................. 604/102 |
| 5,410,797 A | 5/1995 | Steinke et al. ................ 29/435 |
| 5,425,711 A | 6/1995 | Ressemann et al. ......... 604/96 |
| 5,451,233 A | 9/1995 | Yock .......................... 606/194 |
| 5,458,613 A | 10/1995 | Gharibadeh et al. ........ 606/194 |

(List continued on next page.)

FOREIGN PATENT DOCUMENTS

| | | | |
|---|---|---|---|
| DE | 41 04 092 A1 | 8/1991 | ........... A61B/17/34 |
| EP | 0 680 351 B1 | 8/1992 | |
| EP | 1 120 129 A1 | 10/1999 | ........... A61M/25/00 |
| GB | 2319 183 A | 5/1998 | ........... A61M/16/04 |
| WO | WO 93/15872 | 8/1993 | ........... B23P/17/00 |
| WO | WO 00/13733 | 3/2000 | |
| WO | WO 00/25849 | 5/2000 | ........... A61M/25/00 |
| WO | WO 00/33910 | 6/2000 | ........... A61M/25/10 |
| WO | WO 01/05210 A2 | 1/2001 | |

*Primary Examiner*—Teresa Walberg
*Assistant Examiner*—Leonid M Fastovsky
(74) *Attorney, Agent, or Firm*—Crompton, Seager & Tufte LLC

(57) ABSTRACT

A catheter shaft in accordance with one embodiment of the present invention comprises a support member including a distal end, a proximal end, and a plurality of elongate flanges extending therebetween. Each elongate flange has a fixed end and a free end. The fixed end of each flange being fixed to a central portion of the elongate support member. In a preferred embodiment, a sheath is disposed about the support member of the catheter shaft.

61 Claims, 15 Drawing Sheets

U.S. PATENT DOCUMENTS

| | | | |
|---|---|---|---|
| 5,490,837 A | 2/1996 | Blaeser et al. | 604/96 |
| 5,490,845 A | 2/1996 | Racz | 604/266 |
| 5,496,344 A | 3/1996 | Kanesaka et al. | 606/191 |
| 5,496,346 A | 3/1996 | Horzewski et al. | 606/194 |
| 5,522,818 A | 6/1996 | Keith et al. | 604/102 |
| 5,531,690 A | 7/1996 | Solar | 604/102 |
| 5,531,719 A | 7/1996 | Takahashi | 604/280 |
| 5,533,968 A | 7/1996 | Muni et al. | 604/96 |
| 5,556,382 A | 9/1996 | Adams | 604/96 |
| 5,569,200 A | 10/1996 | Umeno et al. | 604/96 |
| 5,573,520 A | 11/1996 | Schwartz et al. | 604/282 |
| 5,578,009 A | 11/1996 | Kraus et al. | 604/96 |
| 5,637,902 A | 6/1997 | Jiang | 257/379 |
| 5,658,251 A | 8/1997 | Ressemann et al. | 604/102 |
| 5,700,253 A | 12/1997 | Parker | 604/282 |
| 5,718,683 A | 2/1998 | Ressemann et al. | 604/96 |
| 5,720,724 A | 2/1998 | Ressemann et al. | 604/96 |
| 5,728,067 A | 3/1998 | Enger | 604/102 |
| 5,752,932 A | 5/1998 | Ellis et al. | 604/96 |
| 5,769,868 A | 6/1998 | Yock | 606/194 |
| 5,772,642 A | 6/1998 | Ciamacco, Jr. et al. | 604/280 |
| 5,782,809 A | 7/1998 | Umeno et al. | 604/280 |
| 5,823,996 A | 10/1998 | Sparks | 604/96 |
| 5,827,269 A * | 10/1998 | Saadat | 606/28 |
| 5,919,188 A * | 7/1999 | Shearon et al. | 606/41 |
| 5,980,486 A | 11/1999 | Enger | 604/102 |
| 6,004,291 A | 12/1999 | Ressemann et al. | 604/96 |
| 6,007,522 A * | 12/1999 | Agro et al. | 604/264 |
| 6,017,323 A * | 1/2000 | Chee | 604/96 |
| 6,027,475 A | 2/2000 | Sirhan et al. | 604/96 |
| 6,036,715 A | 3/2000 | Yock | 606/194 |
| 6,346,093 B1 * | 2/2002 | Altman et al. | 604/167.06 |

* cited by examiner

CATHETER SHAFT

FIELD OF THE INVENTION

The present invention relates generally to catheters for performing medical procedures. More particularly, the present invention relates to methods of fabricating catheter shafts.

BACKGROUND OF THE INVENTION

Intravascular catheters are currently utilized in a wide variety of minimally-invasive medical procedures. Generally, an intravascular catheter enables a physician to remotely perform a medical procedure by inserting the catheter into the vascular system of the patient at an easily accessible location and navigating the tip of the catheter to the desired target site. By this method, virtually any target site in the patient's vascular system may be remotely accessed, including the coronary, cerebral, and peripheral vasculature.

Typically, the catheter enters the patient's vasculature at a convenient location such as a blood vessel in the neck or near the groin. Once the distal portion of the catheter has entered the patient's vascular system the physician may urge the distal tip forward by applying longitudinal forces to the proximal portion of the catheter. For the catheter to effectively communicate these longitudinal forces it is desirable that the catheter have a high level of pushability and kink resistance particularly near the proximal end.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that intravascular catheters be very flexible, particularly near the distal end.

While advancing the catheter through the tortuous path of the patients vasculature, physicians often apply torsional forces to the proximal portion of the catheter to aid in steering the catheter. To facilitate the steering process, the distal portion of the catheter may include a plurality of bends or curves. Torsional forces applied on the proximal end must translate to the distal end to aid in steering. It is therefore desirable that the proximal portion of an intravascular catheter have a relatively high level of torquability to facilitate steering.

After the intravascular catheter has been navigated through the patient's vascular system so that its distal end is adjacent the target site, the catheter may be used for various diagnostic and/or therapeutic purposes. One example of a diagnostic use for an intravascular catheter is the delivery of radiopaque contrast solution to enhance fluoroscopic visualization. In this application, the intravascular catheter provides a fluid path leading from a location outside the body to a desired location inside the body of a patient. In order to maintain a fluid path, it is desirable that intravascular catheters be sufficiently resistant to kinking. In addition, because such fluids are delivered under pressure, it is also desirable that intravascular catheters be sufficiently resistant to bursting or leaking.

Examples of therapeutic purposes for intravascular catheters include percutaneous transluminal angioplasty (PTA) and percutaneous transluminal coronary angioplasty (PTCA). These angioplasty techniques typically involve the use of a guide catheter and a balloon catheter. During these procedures, the distal end of the guide catheter is typically inserted into the femoral artery located near the groin of the patient. The guide catheter is urged through the vasculature of the patient until its distal end is proximate the restriction. In many cases, the distal end of the guide catheter is positioned in the ostium of the coronary artery. The balloon catheter may then be fed through a lumen in the guide catheter such that the balloon is positioned proximate a restriction in a diseased vessel. The balloon is then inflated and the restriction in the vessel is opened. In this application, it is desirable that the guide catheter provide a low friction path for the balloon catheter. The balloon is inflated by urging a liquid though the elongate shaft of the balloon catheter and into the balloon. In this application, the balloon catheter must provide an unobstructed path for the inflation fluid. It is also desirable that the catheter be substantially free of leaks.

As described at length above, it is desirable to combine a number of performance features in an intravascular catheter. It is desirable that the catheter have a relatively high level of pushability and torqueability, particularly near its proximal end. It is also desirable that a catheter be relatively flexible, particularly near it's distal end. The need for this combination of performance features is often addressed by building a catheter which has two or more discrete tubular members having different performance characteristics. For example, a relatively flexible distal section may be spliced to a relatively rigid proximal section. When a catheter is formed from two or more discrete tubular members, it is often necessary to form a bond between the distal end of one tubular member and the proximal end of another tubular member.

Intravascular catheters are often used in conjunction with a guidewire. When this is the case, the guidewire may be advanced through the patient's vasculature until its distal tip has reached a desired target location. Once the distal portion of the guidewire is proximate the desired location, the catheter may be threaded onto the guidewire and urged distally until the distal end of the catheter is proximate the target location.

Intravascular catheters adapted for use with a guidewire typically fall into one of two categories: the over-the-wire category or the single operator exchange (SOE) category. An over-the wire type of catheter includes a guidewire lumen extending from the distal tip of the catheter to the proximal end of the catheter. Whereas, a single operator exchange catheter typically includes a relatively short guidewire lumen proximate the distal end of the catheter.

Single operator exchange catheters were developed in response to difficulties encountered when exchanging over-the-wire catheters. Generally, it is desirable to leave the guidewire in place while a first catheter is withdrawn from the patient and replaced with a second catheter. Maintaining the position of the guidewire tip during the procedure aids the physician in quickly positioning the distal end of the second catheter proximate the target area.

In order to keep the guidewire tip near the target area, the guidewire must be held in place throughout the catheter exchange procedure. A portion of the guidewire is typically grasped by the physician in order to withdraw the first catheter while maintaining distal end of the guidewire in the desired position. To properly anchor the guidewire, a portion of the guidewire must be exposed at all times so it is available for the physician to grasp. In the case of an over-the-wire catheter, this requires that the length of the guidewire extending beyond the patient's body be longer than the catheters. In some cases, length must be added to the guidewire using a guidewire extension. In many cases intravascular catheters are longer than 200 cm. Correspondingly, there may be more than 200 cm of wire extending from the patient. Managing this length of wire during a catheter exchange procedure is awkward, and typically requires two persons. In particular, contamination must be avoided by assuring that the guidewire is not dropped from the sterile field.

An SOE catheter, on the other hand, has a relatively short guidewire wire lumen proximate its distal tip. The length of guidewire extending beyond the body of the patient need only be slightly longer than the guidewire lumen of the catheter. The physician may anchor or hold the guidewire as the first catheter is removed from the body with the exchange occurring over the shorter guidewire lumen. The guidewire lumen of an SOE catheter typically includes a distal guidewire port disposed at the distal tip of the catheter and a proximal guidewire port disposed proximally of the distal end of the catheter. It is desirable to fabricate an SOE catheter, to include a proximal guidewire port, while maintaining the other desirable performance features described previously.

SUMMARY OF THE INVENTION

The present invention relates generally to catheters for performing medical procedures. More particularly, the present invention relates to catheters having a shaft including one or more elongate support members. An elongate support member in accordance with one embodiment of the present invention comprises a first flange, a second flange, and a central member extending between the first flange and the second flange. The first flange and the second flange define an elongate channel having an elongate opening. An inflation conduit defining an inflation lumen is disposed in elongate channel. During the assembly of proximal shaft portion, the inflation conduit may be passed through elongate opening and laid in the elongate channel. In a preferred embodiment, a sheath is disposed about the elongate support member and the inflation conduit. Also in a preferred embodiment, the first flange and the second flange of the elongate support member each have a free end proximate the elongate opening of the elongate channel and a fixed end which is fixed to the central member of the elongate support member.

In a preferred embodiment, the elongate support member is comprised of a metal such as stainless steel, nickel titanium alloys, other alloys, etc. Also in a preferred embodiment, the elongate support member may absorb the energy of bending through deformation of the first flange and the second flange. In a particularly preferred embodiment, the free end of the first flange is free to move relative to the free end of the second flange. Bending energy applied to the elongate support member may be absorbed as the free end of the first flange and the free end of the second flange move relative to one another. The ability of the elongate support member to absorb bending energy may enhance the kink resistance, fracture resistance, and/or toughness of a catheter including the elongate support member.

The elongate support member, preferably, includes a right portion comprising one or more flanges extending beyond a right side of a first central plane extending through a longitudinal axis of the elongate support member and a left portion comprising one or more flanges extending beyond a left side of the first central plane. Additionally, the elongate support member includes a ventral portion comprising one or more flanges extending beyond a ventral side of a second central plane extending through a longitudinal axis of the elongate support member and a dorsal portion comprising one or more flanges extending beyond a dorsal side of the second central plane.

In a preferred embodiment, the right portion has a transverse cross sectional area which is substantially equal to a transverse cross sectional area of the left portion. Also in a preferred embodiment, the ventral portion has a transverse cross sectional area which is substantially equal to a transverse cross sectional area of the dorsal portion. In a particularly preferred embodiment, the transverse cross sectional area the ventral portion, the transverse cross sectional area the dorsal portion, the transverse cross sectional area the right portion, and the transverse cross sectional area the left portion are all substantially equal.

In a preferred embodiment, the elongate support member resists bending along the first central plane. Also in a preferred embodiment, the elongate support member resists bending along the second central plane. In a particularly preferred embodiment, the resistance of the elongate support member to bending along second central plane is substantially equal to it's resistance to bending along first central plane. The non-preferential resistance to bending of the elongate support member may enhance the pushability and kink resistance of a catheter including the elongate support member.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
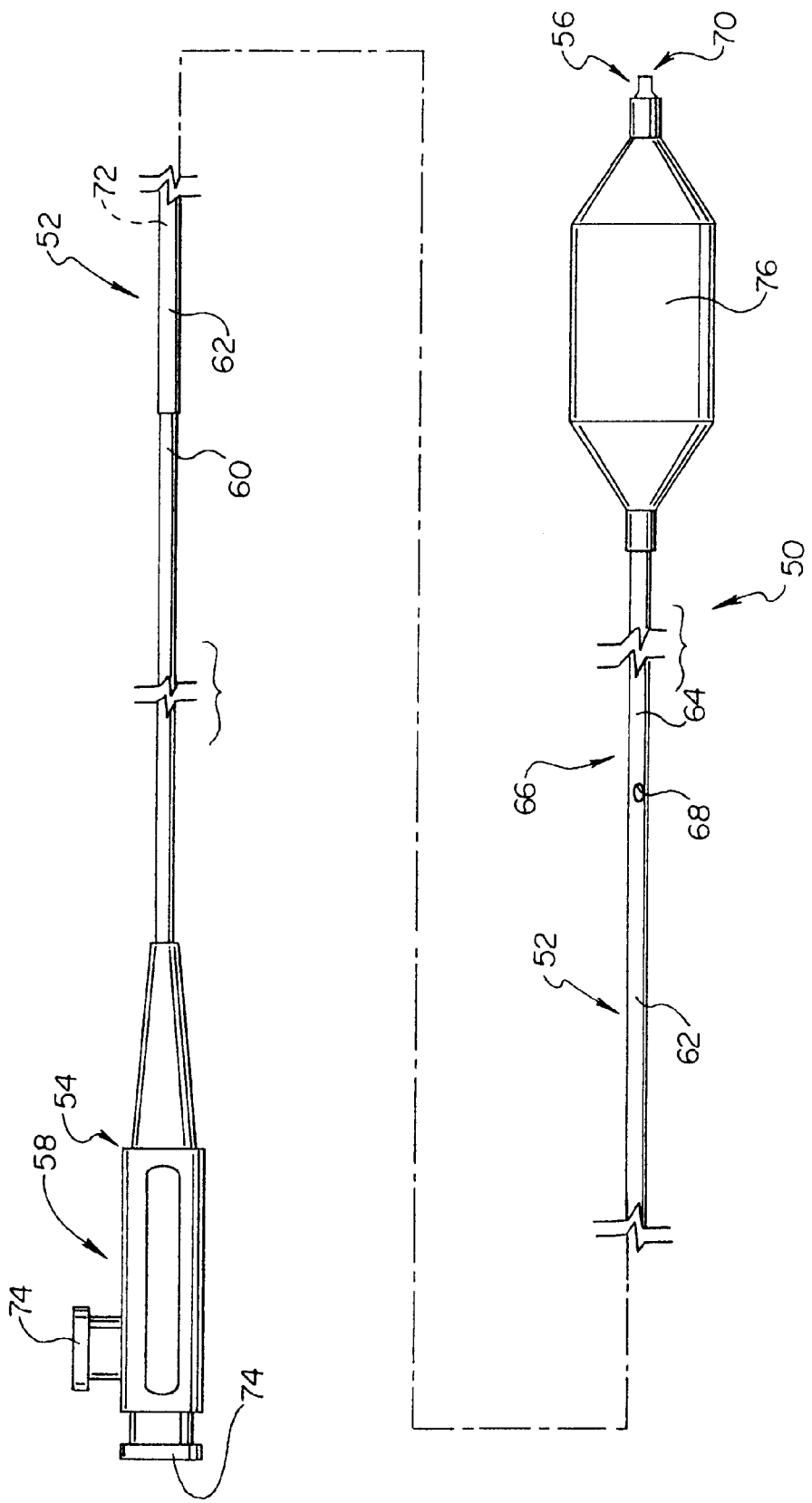
FIG. 1 is a plan view of a catheter in accordance with an exemplary embodiment of the present invention.

FIG. 1 is a plan view of a catheter 50 in accordance with an exemplary embodiment of the present invention. Catheter 50 includes an elongate shaft 52 having a distal end 56 and a proximal end 54. A hub assembly 58 is disposed about elongate shaft 52, proximate proximal end 54 thereof. Hub assembly 58 includes a plurality of hub ports 74.

Elongate shaft 52 includes a proximal shaft portion 60, a middle shaft portion 62, and a distal shaft portion 64. Proximal shaft portion 60, middle shaft portion 62, and distal shaft portion 64 each have a proximal end and a distal end. As shown in FIG. 1, the distal end of proximal shaft portion 60 is fixed to the proximal end of middle shaft portion 62. Likewise, the distal end of middle shaft portion 62 is fixed to the proximal end of distal shaft portion 64 proximate a transition region 66. It is to be appreciated that catheter 50 may include more or less than three shaft portions without deviating from the spirit and scope of the present invention.

In the embodiment of FIG. 1, elongate shaft 52 of catheter 50 defines a proximal guidewire port 68. Catheter 50 also includes a distal guidewire port 70 disposed proximate distal end 56 of elongate shaft 52. Elongate shaft 52 includes a plurality of walls defining a guidewire lumen (not shown) which is in fluid communication with proximal guidewire port 68 and distal guidewire port 70.

Elongate shaft 52 also includes a plurality of walls defining an inflation lumen 72. Inflation lumen 72 is in fluid communication with a hub port 74 of hub assembly 58 and a balloon 76 disposed about elongate shaft 52 proximate distal end 56. Hub port 74 of hub assembly 58 is adapted to couple with a fluid source. Balloon 76 may be inflated by urging fluid from the fluid source into balloon 76 via inflation lumen 72. Catheter 50 of FIG. 1 is a type of catheter which may be generally referred to as a balloon catheter. It is to be appreciated that methods and devices in accordance with the present invention may be used in conjunction with other types of catheter without deviating from the spirit and scope of the present invention.

Figure 2A:
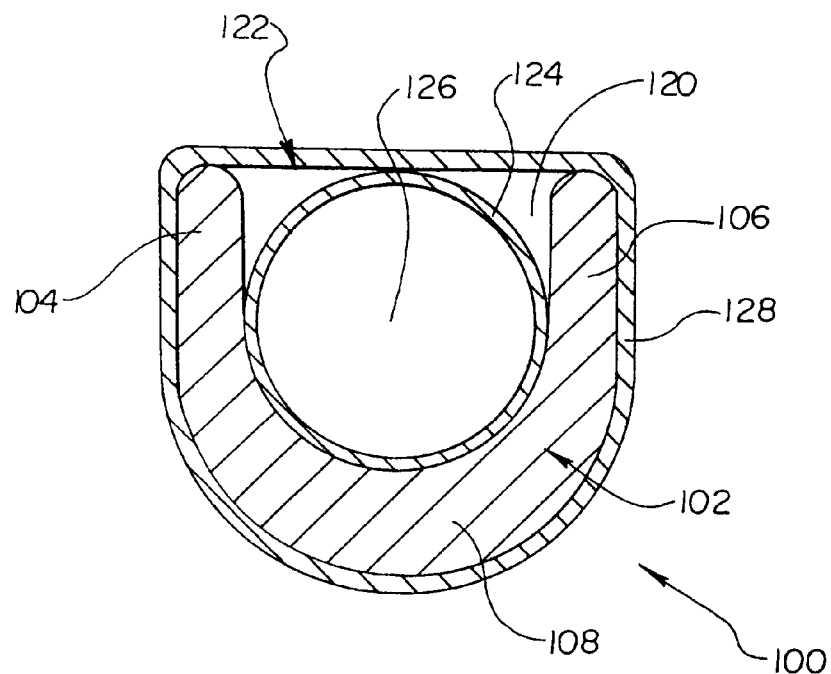
FIG. 2A is a transverse cross-sectional view of an exemplary embodiment of a catheter shaft including an elongate support member in accordance with the present invention.

FIG. 2A is a transverse cross-sectional view of an exemplary embodiment of a catheter shaft 100 in accordance with the present invention. Catheter shaft 100 may form, for example, a portion of elongate shaft 52 of catheter 50. In a preferred embodiment, proximal shaft portion 60 of elongate shaft 52 of catheter 50 comprises catheter shaft 100. Catheter shaft 100 includes an elongate support member 102 comprising a first flange 104, a second flange 106, and a central member 108 extending between first flange 104 and second flange 106. First flange 104 and a second flange 106 define an elongate channel 120 having an elongate opening 122. An inflation conduit 124 defining an inflation lumen 126 is disposed in elongate channel 120. During the assembly of catheter shaft 100, inflation conduit 124 may be passed through elongate opening 122 and laid in elongate channel 120. A sheath 128 is disposed about elongate support member 102 and inflation conduit 124.

Figure 2B:
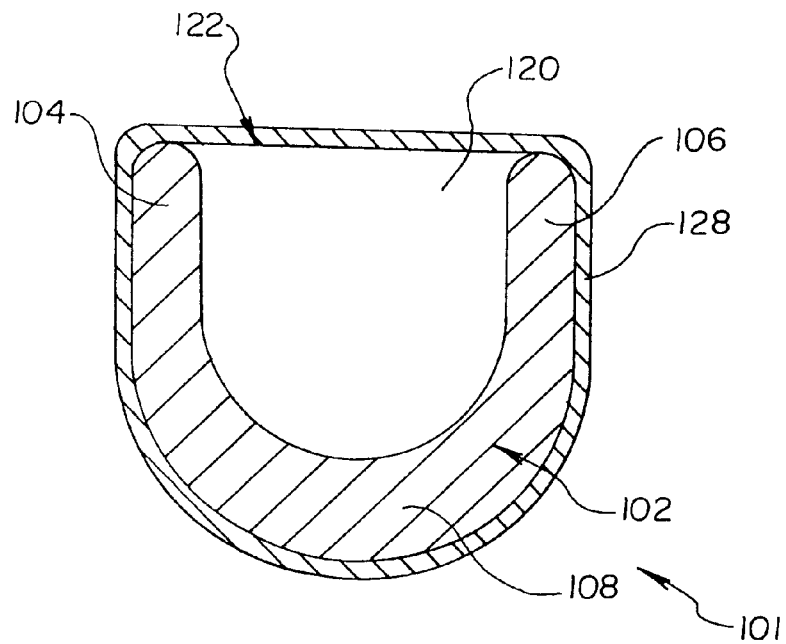
FIG. 2B is a transverse cross-sectional view of an exemplary embodiment of a catheter shaft including an elongate support member in accordance with the present invention.

FIG. 2B is a transverse cross-sectional view of an additional exemplary embodiment of a catheter shaft 101 in accordance with the present invention. Catheter shaft 101 includes an elongate support member 102 comprising a first flange 104, a second flange 106, and a central member 108 extending between first flange 104 and second flange 106. First flange 104 and a second flange 106 define an elongate channel 120 having an elongate opening 122. A sheath 128 is disposed about elongate support member 102 and inflation conduit 124.

Figure 3:
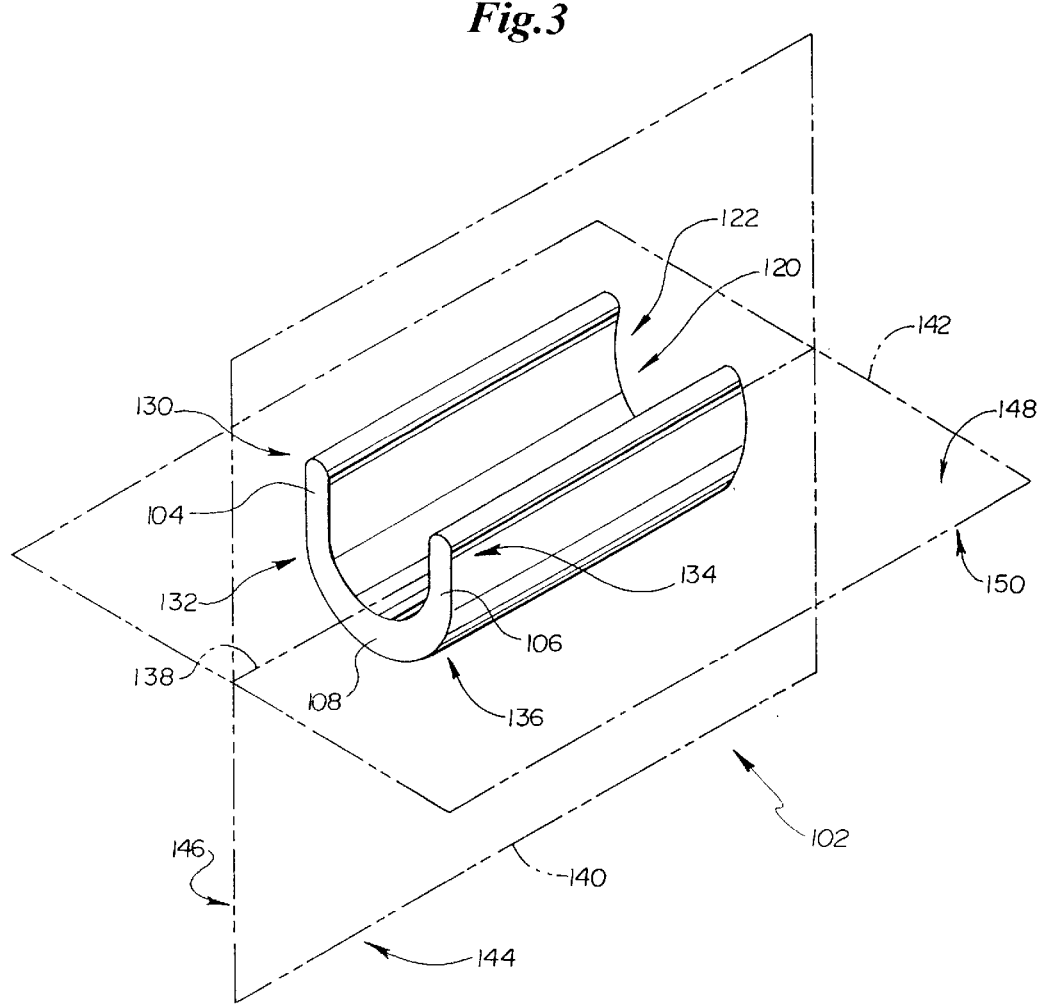
FIG. 3 is a perspective view of a portion of the elongate support member of the catheter shafts of FIG. 2A and FIG. 2B.

FIG. 3 is a perspective view of a portion of elongate support member 102 of catheter shaft 100. In FIG. 3 it may be appreciated that first flange 104 of elongate support member 102 has a free end 130 proximate elongate opening 122 of elongate channel 120 and a fixed end 132 which is fixed to central member 108 of elongate support member 102. Likewise, second flange 106 of elongate support member 102 has a free end 134 proximate elongate opening 122 of elongate channel 120 and a fixed end 136 which is fixed to central member 108 of elongate support member 102.

Elongate support member 102 has a longitudinal axis 138 which is shown as a dashed line in FIG. 3. In a preferred embodiment, longitudinal axis 138 extends through the center of gravity of elongate support member 102. A first central plane 140 is also shown with dashed lines in FIG. 3. First central plane 140 extends through longitudinal axis 138 of elongate support member 102. First central plane 140 has a right side 144 and a left side 146. A second central plane 142 also extends through longitudinal axis 138 of elongate support member 102 and intersects first central plane 140. In the embodiment of FIG. 3, second central plane 142 is disposed at a 90 degree angle to first central plane 140. Second central plane 142 has a ventral side 150 and a dorsal side 148.

Figure 4:
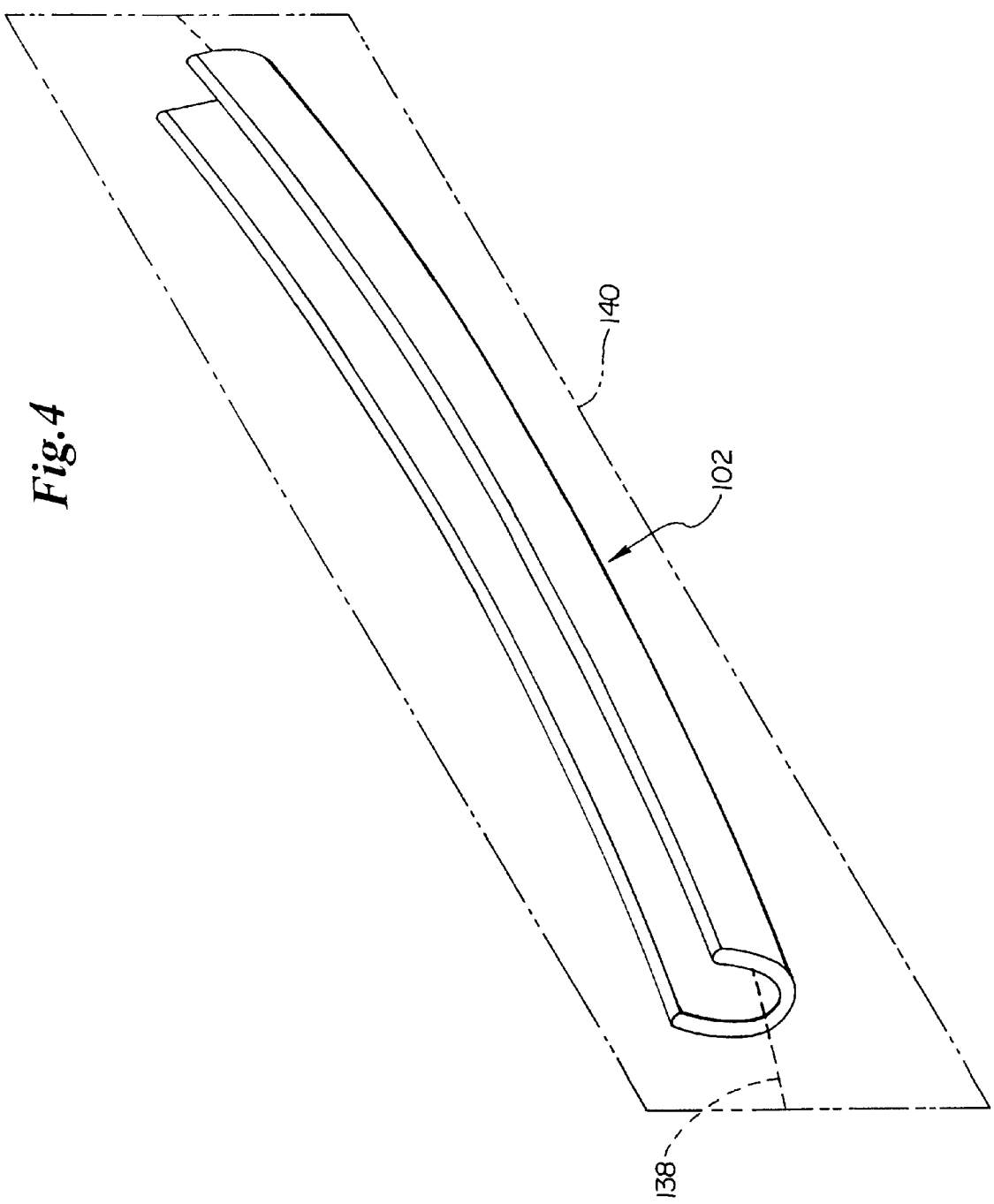
FIG. 4 is a perspective view of a portion of an elongate support member in accordance with an exemplary embodiment of the present invention which is bent along a first central plane.

FIG. 4 is a perspective view of a portion of elongate support member 102 which is bent along first central plane 140. In the embodiment of FIG. 4, elongate support member 102 is bent so that longitudinal axis 138 of elongate support member 102 defines a plane which is coplanar with first central plane 140. The bending of elongate support member 102 illustrated in FIG. 4 is preferably elastic bending. In the case of elastic bending, elongate support member 102 will return to substantially the shape shown in FIG. 3 when the bending forces are removed. Another type of bending is plastic bending. In the case of plastic bending, at least a portion of the deformation caused by the bending forces will remain after the bending forces are removed.

In a preferred embodiment, elongate support member 102 resists bending along first central plane 140. Also in a preferred embodiment, elongate support member 102 resists bending along second central plane 142 shown in FIG. 3. In a particularly preferred embodiment, the resistance of elongate support member 102 to bending along second central plane 142 is substantially equal to it's resistance to bending along first central plane 140. The non-preferential resistance to bending of elongate support member 102 may enhance the pushability and kink resistance of a catheter including elongate support member 102.

Figure 5:
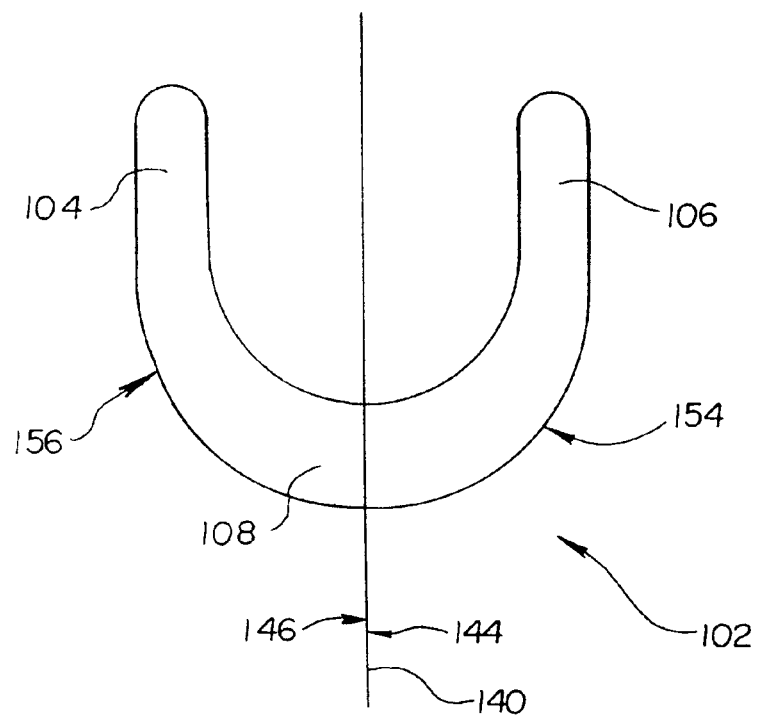
FIG. 5 is a transverse cross-sectional view of an elongate support member in accordance with an exemplary embodiment of the present invention and a first central plane dividing the elongate support member into a right portion and a left portion.

FIG. 5 is a transverse cross-sectional view of elongate support member 102 and first central plane 140. In FIG. 5 it may be appreciated that first central plane 140 divides elongate support member 102 into a right portion 154 extending beyond right side 144 of first central plane 140 and a left portion 156 extending beyond left side 146 of first central plane 140. In the embodiment of FIG. 5, left portion 156 of elongate support member 102 comprises first flange 104 and a portion of central member 108. Likewise, right portion 154 comprises second flange 106 and a portion of central member 108. In a preferred embodiment, right portion 154 has a transverse cross sectional area which is substantially equal to the transverse cross sectional area of left portion 156. In the embodiment of FIG. 5, elongate support member 102 is generally symmetrical about the first central plane 140.

Figure 6:
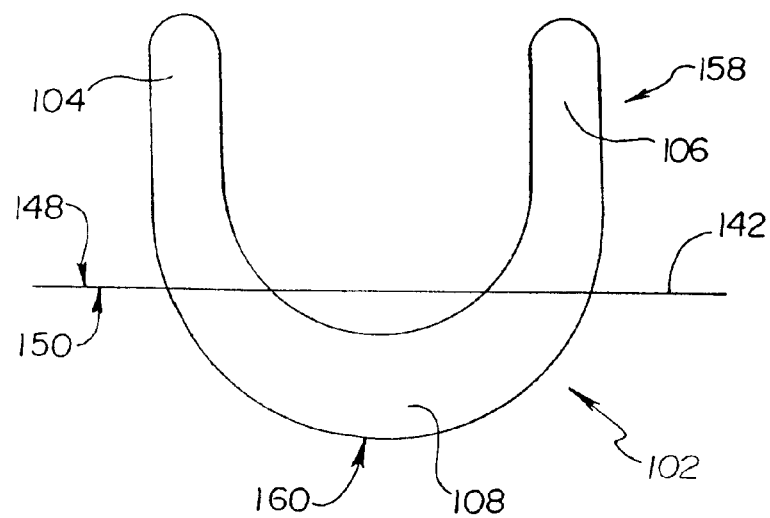
FIG. 6 is a transverse cross-sectional view of an elongate support member in accordance with an exemplary embodiment of the present invention and a second central plane dividing the elongate support member into a dorsal portion and a ventral portion.

FIG. 6 is a transverse cross-sectional view of elongate support member 102 and second central plane 142. In FIG. 6 it may be appreciated that second central plane 142 divides elongate support member 102 into a ventral portion 160 and a dorsal portion 158. Ventral portion 160 extends beyond ventral side 150 of second central plane 142 and dorsal portion 158 extends beyond dorsal side 148 of second central plane 142.

In the embodiment of FIG. 6, dorsal portion 158 of elongate support member 102 comprises a portion of first flange 104 and a portion of second flange 106. Ventral portion 160 of elongate support member 102 comprises a portion of first flange 104, a portion of second flange 106, and central member 108. In a preferred embodiment, ventral portion 160 has a transverse cross sectional area which is substantially equal to the transverse cross sectional area of dorsal portion 158. In the embodiment of FIG. 6, elongate support member 102 is generally asymmetrical about second central plane 142.

Figure 7:
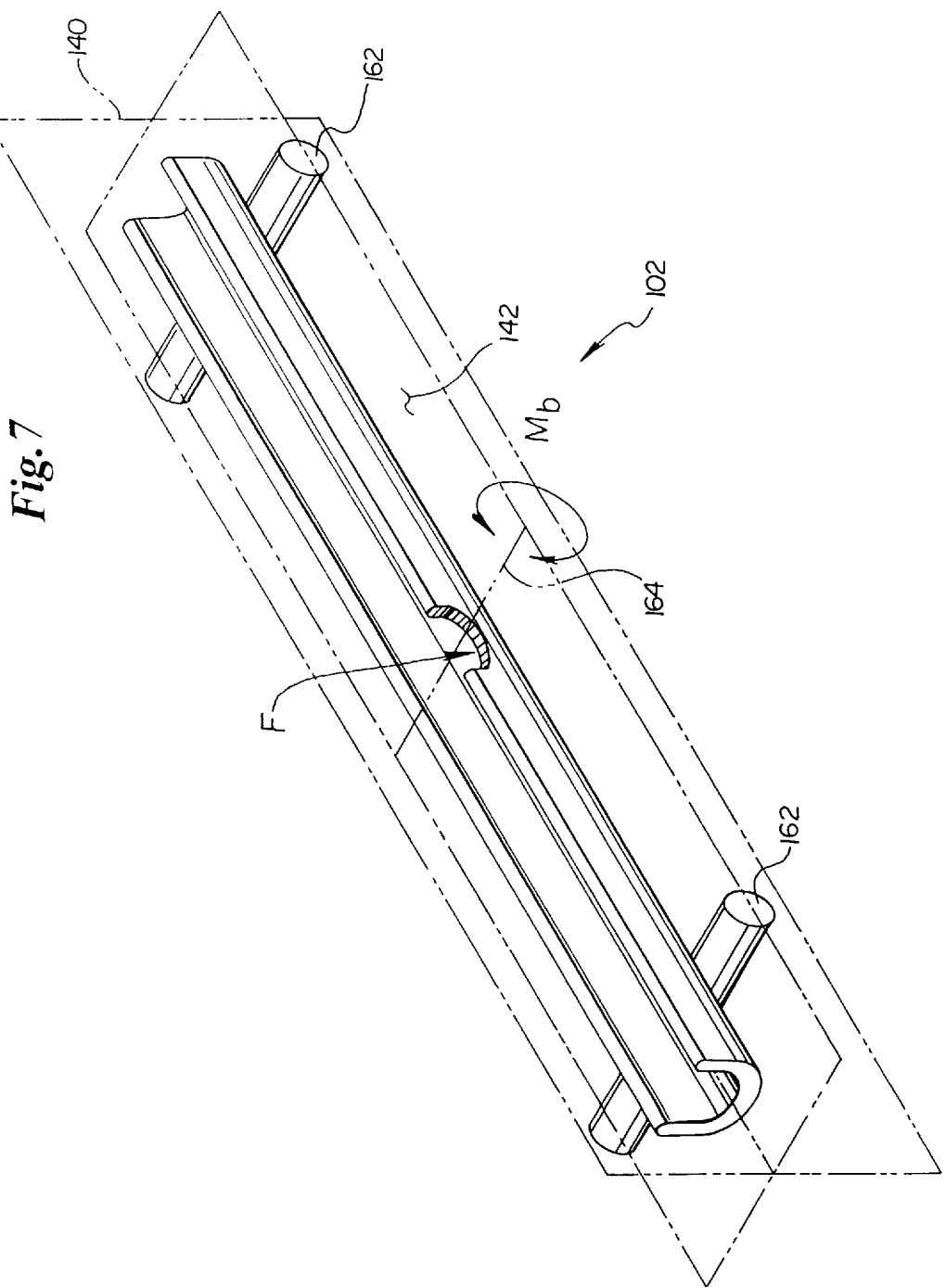
FIG. 7 is a perspective view of a segment of an elongate support member in accordance with an exemplary embodiment of the present invention resting on two supports, a force F is shown acting on the elongate support member approximately midway between the supports resulting in a bending moment $M_b$ acting about a first bending axis.

FIG. 7 is a perspective view of a segment of elongate support member 102 resting on two supports 162. A force F is shown acting on elongate support member 102 approximately midway between supports 162. The application of force F to elongate support member 102 results in a bending moment $M_b$ acting about a first bending axis 164. In the embodiment of FIG. 7, first bending axis 164 lies in second central plane 142. Bending moment $M_b$ may result in bending along first central plane 140.

Figure 8:
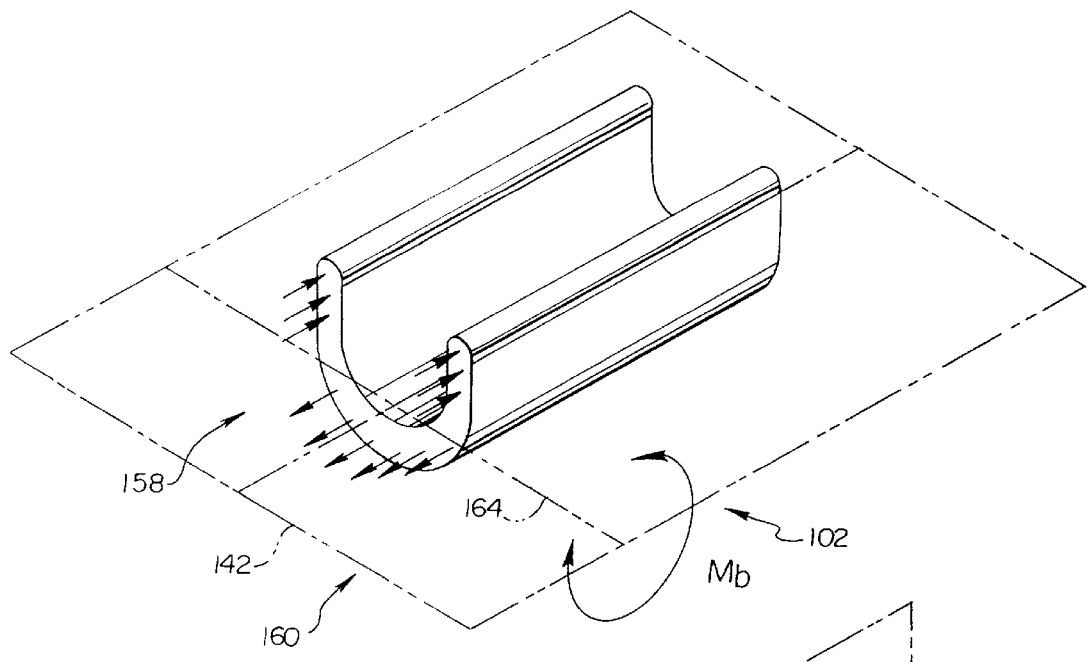
FIG. 8 is an enlarged cross sectional view of a portion of the elongate support member of FIG. 7 taken along a sectional plane extending through the first bending axis.

FIG. 8 is an enlarged cross sectional view of a portion of elongate support member 102 taken along a sectional plane which extends through first bending axis 164. Second central plane 142 is also illustrated in FIG. 8, as describe previously, second central plane 142 divides elongate support member 102 into a dorsal portion 158 and a ventral portion 160. As illustrated in FIG. 8, bending moment $M_b$ places dorsal portion 158 of elongate support member 102 in compression. Bending moment $M_b$ also places ventral portion 160 of elongate support member 102 in tension. As described previously, ventral portion 160, preferably, has a transverse cross sectional area which is substantially equal to the transverse cross sectional area of dorsal portion 158. Thus, in the embodiment of FIG. 8, the area of elongate support member 102 in compression is substantially equal to the area of elongate support member 102 in tension. In this preferred embodiment, second central plane 142 comprises a neutral plane when support member 102 is bent along first central plane 140.

Figure 9:
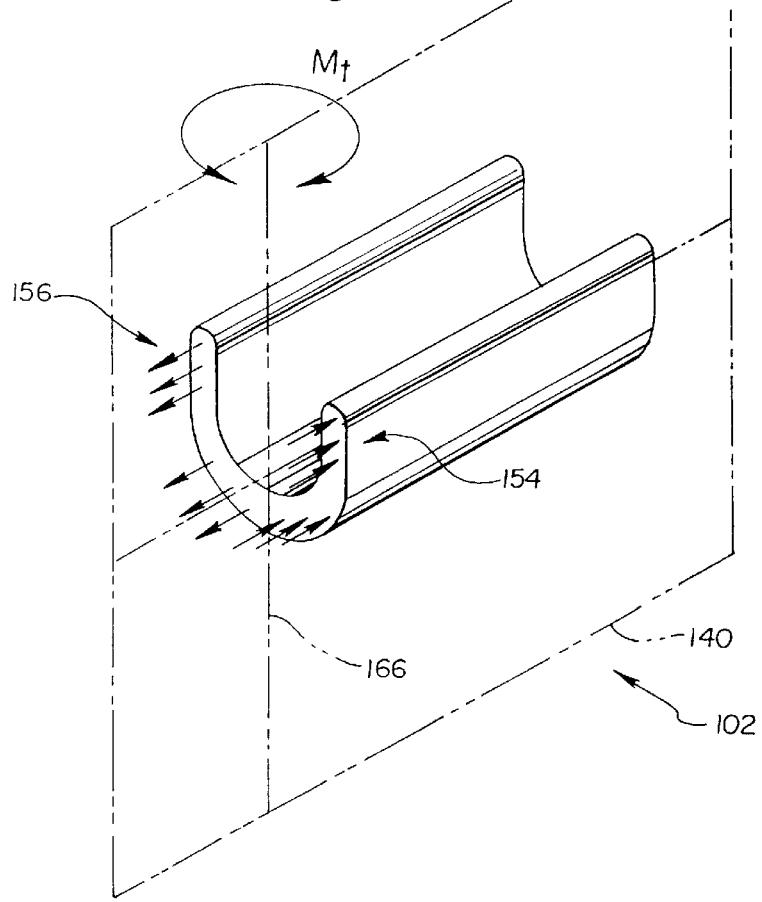
FIG. 9 is a cross sectional perspective view of a portion of elongate support member taken through a sectional plane extending through a second bending axis.

FIG. 9 is a cross sectional perspective view of a portion of elongate support member 102 taken through a sectional plane which extends through a second bending axis 166. In the embodiment of FIG. 9, second bending axis 166 lies in first central plane 140. As described previously, first central plane 140 divides elongate support member 102 into a right portion 154 and a left portion 156. In the embodiment of FIG. 9, a bending moment $M_b$ is acting on elongate support member 102. As illustrated in FIG. 9, bending moment $M_b$ places right portion 154 of elongate support member 102 in compression. Bending moment $M_b$ also places left portion 156 of elongate support member 102 in tension.

As described previously, right portion 154 preferably has a transverse cross sectional area which is substantially equal to the transverse cross sectional area of left portion 156. Thus, in the embodiment of FIG. 9, the area of elongate support member 102 in compression is substantially equal to the area of elongate support member 102 in tension. In this preferred embodiment, first central plane 140 comprises a neutral plane when support member 102 is bent along second central plane 142.

In a particularly preferred embodiment, the transverse cross sectional areas of left portion 156, right portion 154, ventral portion 160, and dorsal portion 158 are all substantially equal. In this particularly preferred embodiment, the resistance of elongate support member 102 to bending along second central plane 142 is substantially equal to the bend resistance of elongate support member 102 along first central plane 140. This non-preferential resistance to bending may enhance the pushability and kink resistance of a catheter including elongate support member 102.

Figure 10:
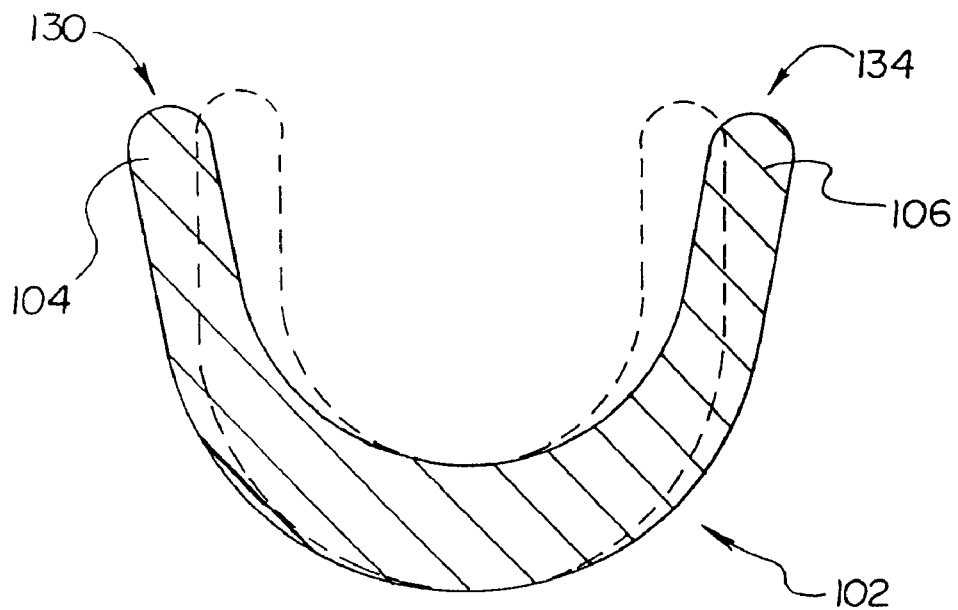
FIG. 10 is a transverse cross-sectional view of an elongate support member in a first deflected state in accordance with an exemplary embodiment of the present invention.

FIG. 10 is a transverse cross-sectional view of elongate support member 102 in a first deflected state. In the embodiment of FIG. 10, first flange 104 and second flange 106 are outwardly deflected relative to one another. In a preferred embodiment, elongate support member 102 is comprised of a somewhat springy material. Also in a preferred embodiment, elongate support member 102 may absorb the energy of bending through deformation of first flange 104 and second flange 106. The deformation may be elastic deformation or plastic deformation. Plastic deformation is deformation which will remain after the force creating the deformation is removed. Elastic deformation is deformation which disappears when the external forces are removed. The undeflected shape of elongate support member 102 is shown with hidden lines in FIG. 10.

During deflection, free end 130 of first flange 104 is free to move relative to free end 134 of second flange 106. Bending energy applied to elongate support member 102 may be absorbed as free end 130 of first flange 104 and free end 134 of second flange 106 move relative to one another. The ability of elongate support member 102 to absorb bending energy may enhance the kink resistance, fracture resistance, and/or toughness of a catheter including elongate support member 102.

Figure 11:
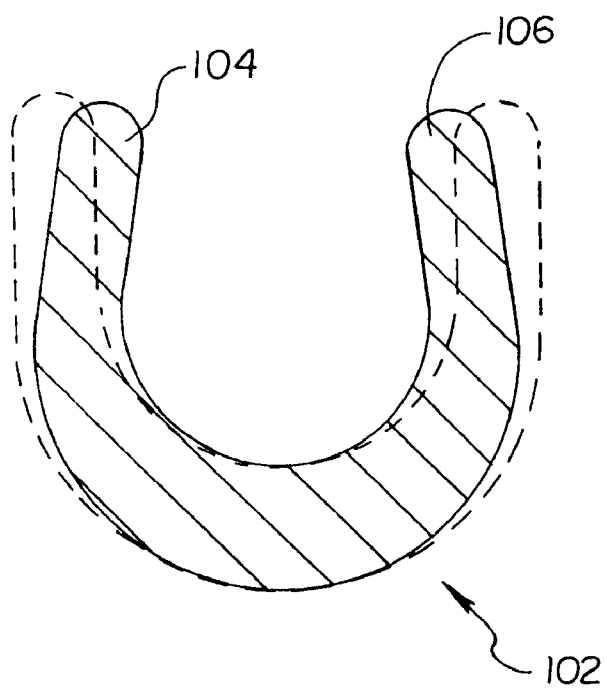
FIG. 11 is a transverse cross-sectional view of an elongate support member in a second deflected state in accordance with an exemplary embodiment of the present invention.

FIG. 11 is a transverse cross-sectional view of elongate support member 102 in a second deflected state. In the embodiment of FIG. 11, first flange 104 and second flange 106 are deflected inward relative to one another. The undeflected shape of elongate support member 102 is shown with hidden lines in FIG. 11.

Figure 12:
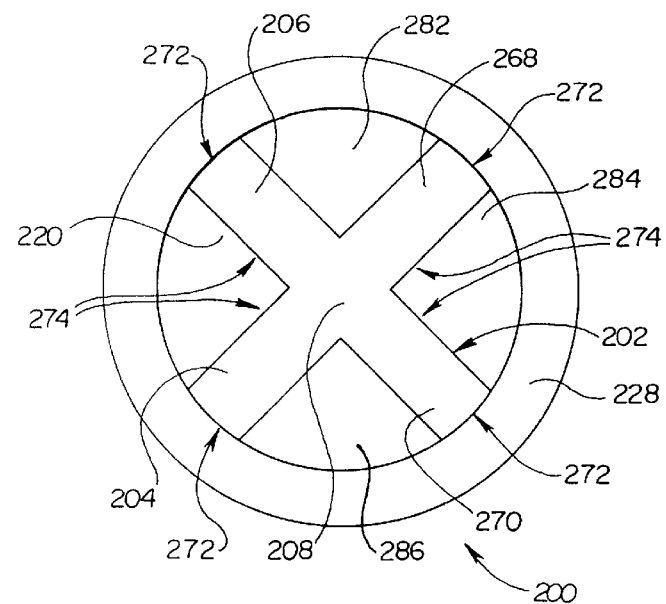
FIG. 12 is a transverse cross-sectional view of an additional exemplary embodiment of a catheter shaft including an elongate support member in accordance with the present invention.

FIG. 12 is a transverse cross-sectional view of an additional exemplary embodiment of a catheter shaft 200 in accordance with the present invention. Catheter shaft 200 includes an elongate support member 202 comprising a first flange 204, a second flange 206, a third flange 268, fourth flange 270, and a central member 208. Each flange includes a free end 272, and a fixed end 274 which is fixed to central member 208. First flange 204 and second flange 206 define a first elongate channel 220. Second flange 206 and third flange 268 define a second elongate channel 282. Third flange 268 and fourth flange 270 define a third elongate channel 284. Fourth flange 270 and first flange 204 define a fourth elongate channel 286. A sheath 228 is disposed about elongate support member 202.

Figure 13:
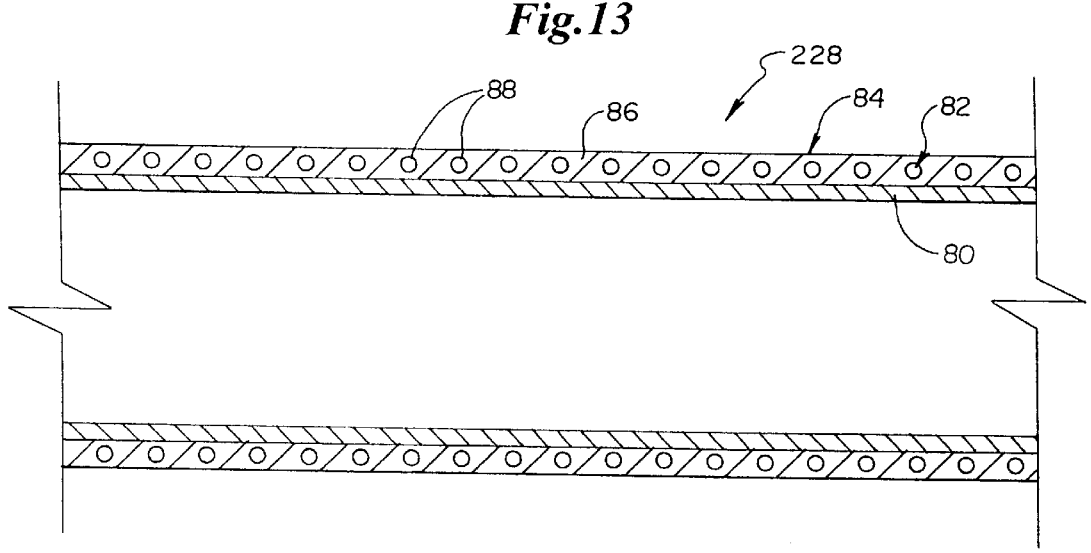
FIG. 13 is a longitudinal cross sectional view of a sheath in accordance with an exemplary embodiment of the present invention.

FIG. 13 is a longitudinal cross sectional view of an exemplary embodiment of sheath 228 of FIG. 12. In the embodiment of FIG. 13, sheath 228 comprises an inner layer 80 which is overlaid by a support matrix 82. A jacket 84 comprising a jacket material 86 overlays support matrix 82. Jacket material 86 of jacket 84 is also disposed within a plurality of interstitial spaces defined by support matrix 82. In the embodiment of FIG. 13, support matrix 82 is comprised of a plurality of filaments 88. In a preferred embodiment, filaments 88 are comprised of stainless steel wire, wound in a braided pattern around inner layer 80. Other embodiments of support matrix 82 are possible without deviating from the spirit and scope of the present invention. For example, support matrix 82 may be comprised of a plurality of polymer filaments braided or knitted together. By way of a second example, support matrix 82 may be comprised of polymer filaments wound in a spiral pattern around inner layer 80.

In a presently preferred embodiment, jacket 84 is comprised of polyether block amide (PEBA). Polyether block amide is commercially available from Atochem Polymers of Birdsboro, Penn. under the trade name PEBAX. Jacket 84 may be fabricated using an extrusion process. In this process, molten PEBA is extruded onto the combined layers of inner layer 80 and support matrix 82. When this process is used, the material of jacket 84 fills any interstitial spaces in support matrix 82.

It is to be understood that other manufacturing processes may be used without departing from the spirit and scope of the present invention. Jacket 84 may also be comprised of other materials without departing from the spirit of scope of this invention. Examples of materials which may be suitable in some applications include: thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), and the like.

Figure 14:
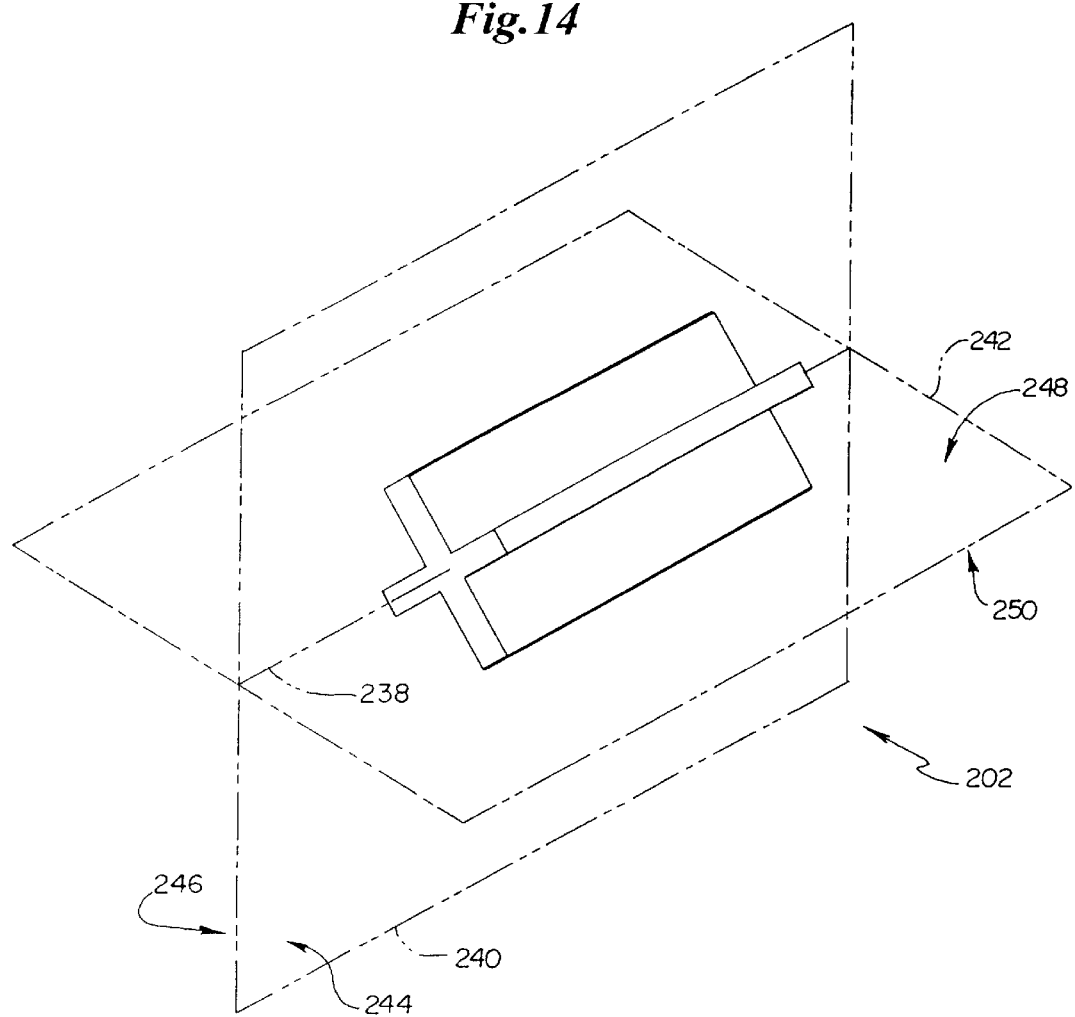
FIG. 14 is a perspective view of a portion of the elongate support member of the catheter shaft of FIG. 12.

FIG. 14 is a perspective view of a portion of elongate support member 202 of FIG. 12. Elongate support member 202 has a longitudinal axis 238 which is shown as a dashed line in FIG. 14. In a preferred embodiment, longitudinal axis 238 extends through the center of gravity of elongate support member 202. A first central plane 240 is also shown with dashed lines in FIG. 14. First central plane 240 extends through longitudinal axis 238 of elongate support member 202. First central plane 240 has a right side 244 and a left side 246. A second central plane 242 also extends through longitudinal axis 238 of elongate support member 202 and intersects first central plane 240. In the embodiment of FIG. 14, second central plane 242 is disposed at a 90 degree angle to first central plane 240. Second central plane 242 has a ventral side 250 and a dorsal side 248.

Figure 15:
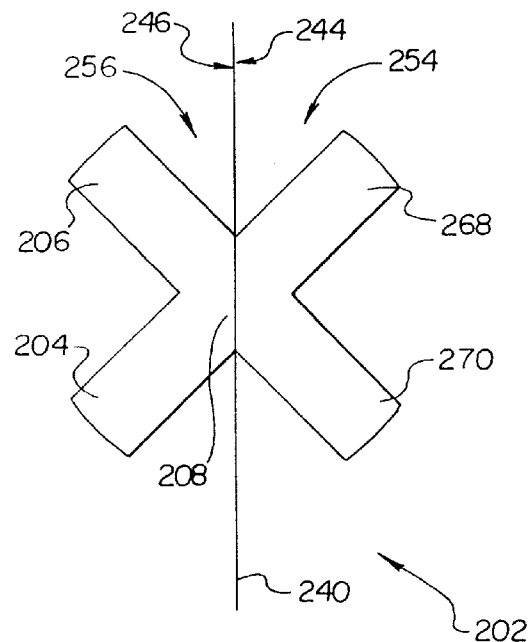
FIG. 15 is a transverse cross-sectional view of an elongate support member in accordance with an exemplary embodiment of the present invention and a first central plane dividing the elongate support member into a right portion and a left portion.

FIG. 15 is a transverse cross-sectional view of elongate support member 202 and first central plane 240. In FIG. 15 it may be appreciated that first central plane 240 divides elongate support member 202 into a right portion 254 extending beyond right side 244 of first central plane 240 and a left portion 256 extending beyond left side 246 of first central plane 240. In the embodiment of FIG. 15, left portion 256 of elongate support member 202 comprises first flange 204, second flange 206, and a portion of central member 208. Right portion 254 comprises third flange 268, fourth flange 270, and a portion of central member 208. In a preferred embodiment, right portion 254 has a transverse cross sectional area which is substantially equal to the transverse cross sectional area of left portion 256.

Figure 16:
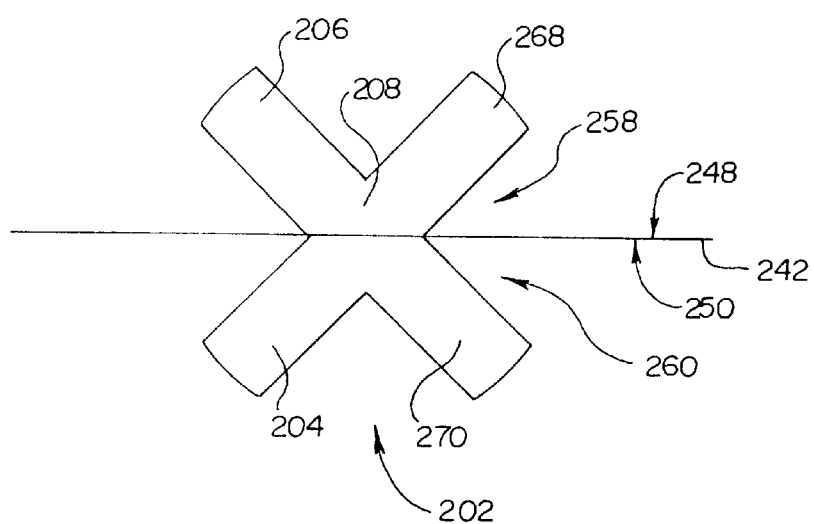
FIG. 16 is a transverse cross-sectional view of an elongate support member in accordance with an exemplary embodiment of the present invention and a second central plane dividing the elongate support member into a dorsal portion and a ventral portion.

FIG. 16 is a transverse cross-sectional view of elongate support member 202 and second central plane 242. In FIG. 16 it may be appreciated that second central plane 242 divides elongate support member 202 into a ventral portion 260 and a dorsal portion 258. Ventral portion 260 extends beyond ventral side 250 of second central plane 242 and dorsal portion 258 extends beyond dorsal side 248 of second central plane 242. In the embodiment of FIG. 16, dorsal portion 258 of elongate support member 202 comprises second flange 206, third flange 268, and a portion of central member 208. Ventral portion 260 of elongate support member 202 comprises first flange 204, fourth flange 270, and a portion of central member 208. In a preferred embodiment, ventral portion 260 has a transverse cross sectional area which is substantially equal to the transverse cross sectional area of dorsal portion 258.

In a particularly preferred embodiment of elongate support member 202, the transverse cross sectional areas of left portion 256, right portion 254, ventral portion 260, and dorsal portion 258 are all substantially equal. In this particularly preferred embodiment, the resistance of elongate support member 202 to bending along second central plane 242 is substantially equal to the bend resistance of elongate support member 202 along first central plane 240. This non-preferential resistance to bending may enhance the pushability and kink resistance of a catheter including elongate support member 202.

Figure 17:
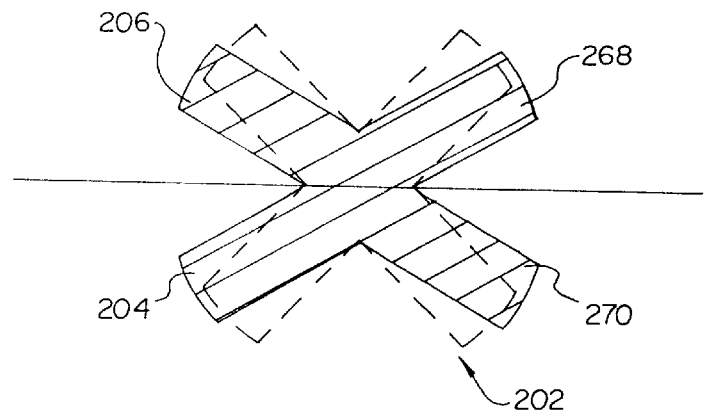
FIG. 17 is a transverse cross-sectional view of an elongate support member in a deflected state in accordance with an exemplary embodiment of the present invention.

FIG. 17 is a transverse cross-sectional view of elongate support member 202 in a deflected state. In the embodiment of FIG. 17, first flange 204 and second flange 206 are inwardly deflected relative to one another. Likewise, third flange 268 and fourth flange 270 are inwardly deflected relative to one another. In a preferred embodiment, elongate support member 202 is comprised of a somewhat springy material. Also in a preferred embodiment, elongate support member 202 may absorb the energy of bending through deformation of first flange 204, second flange 206, third flange 268 and fourth flange 270. The deformation may be elastic deformation or plastic deformation. The undeflected shape of elongate support member 202 is shown with hidden lines in FIG. 17. During deflection, the free ends of the flanges are free to move relative to the fixed ends of the flanges. Bending energy applied to elongate support member 202 may be absorbed as the flanges deform. The ability of elongate support member 202 to absorb bending energy may enhance the kink resistance, fracture resistance, and/or toughness of a catheter including elongate support member 202.

Figure 18:
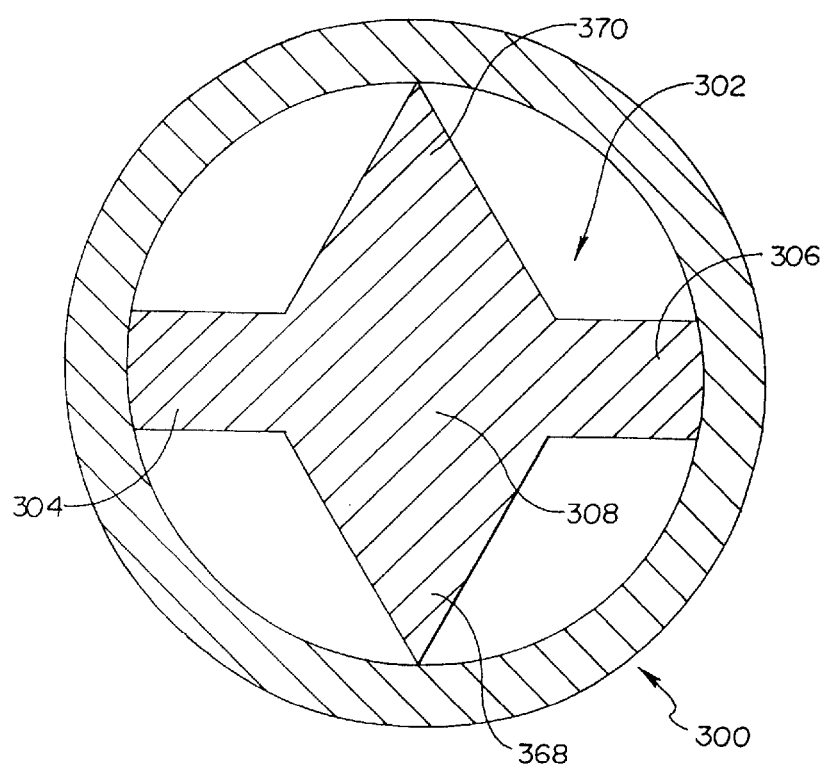
FIG. 18 is a transverse cross-sectional view of an additional exemplary embodiment of a catheter shaft including an elongate support member in accordance with the present invention.

FIG. 18 is a transverse cross-sectional view of an additional exemplary embodiment of catheter shaft 300 in accordance with the present invention. Catheter shaft 300 includes an elongate support member 302 comprising a first flange 304, a second flange 306, a third flange 368, fourth flange 370, and a central member 308. Each flange includes a free end and a fixed end which is fixed to central member 308. In the embodiment of FIG. 18, first flange 304 and second flange 306 each have a generally polyhedral shape with a generally rectangular transverse cross section. Third flange 368 and fourth flange 370 each have a generally polyhedral shape with a generally triangular transverse cross section.

Figure 19:
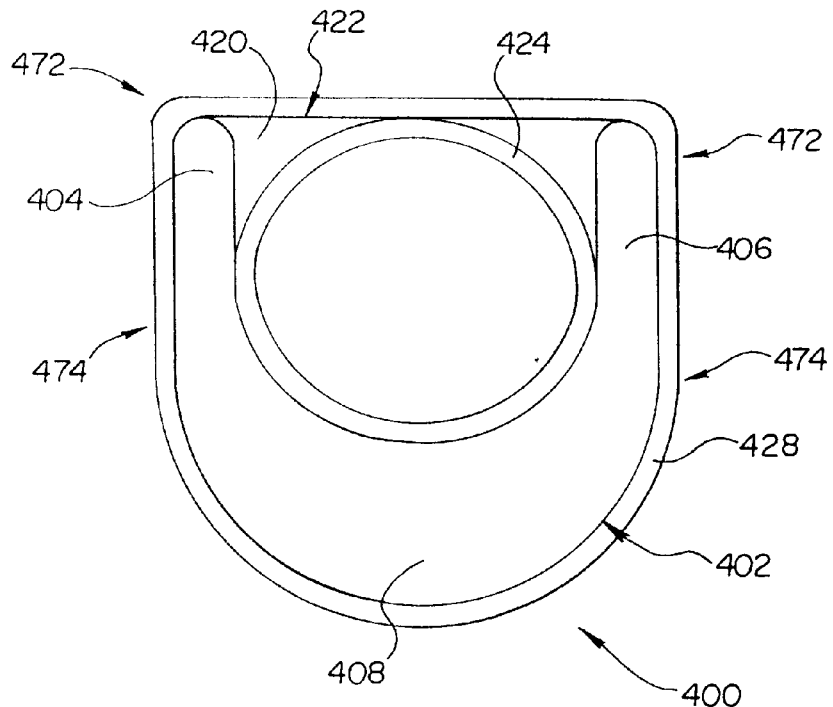
FIG. 19 is a transverse cross-sectional view of an additional exemplary embodiment of a catheter shaft including an elongate support member in accordance with the present invention.

FIG. 19 is a transverse cross-sectional view of an additional exemplary embodiment of catheter shaft 400 in accordance with the present invention. Catheter shaft 400 includes an elongate support member 402, an inflation conduit 424, and a sheath 428 disposed about elongate support member 402 and inflation conduit 424. Elongate support member 402 comprises a first flange 404, a second flange 406, and a central member 408 extending between first flange 404 and second flange 406. First flange 404 and a second flange 406 define an elongate channel 420 having an elongate opening 422. First flange 404 of elongate support member 402 has a free end 472 proximate elongate opening 422 of elongate channel 420 and a fixed end 474 which is fixed to central member 408 of elongate support member 402. Likewise, second flange 406 of elongate support member 402 has a free end 472 proximate elongate opening 422 of elongate channel 420 and a fixed end 474 which is fixed to central member 408 of elongate support member 402. In the embodiment of FIG. 19, central member 408 has a thickness which is substantially greater either the thickness of first flange 404 or the thickness of second flange 406.

Figure 20:
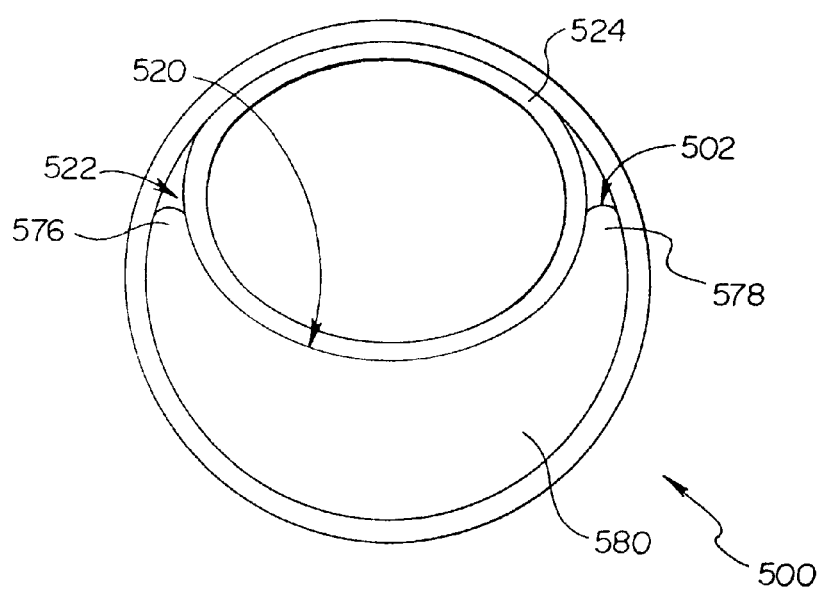
FIG. 20 is a transverse cross-sectional view of an additional exemplary embodiment of a catheter shaft including an elongate support member in accordance with the present invention.

FIG. 20 is a transverse cross-sectional view of an additional exemplary embodiment of catheter shaft 500 in accordance with the present invention. Catheter shaft 500 includes an elongate support member 502, an inflation conduit 524, and a sheath 528 disposed about elongate support member 502 and inflation conduit 524. Elongate support member 502 comprises a first ridge portion 576, a second ridge portion 578, and a central portion 580 extending between first ridge portion 576 and second ridge portion 578. First ridge portion 576, second ridge portion 578, and central portion 580 an elongate channel 520 having an elongate opening 522. Inflation conduit 524 is partially disposed within elongate channel 520.

Figure 21:
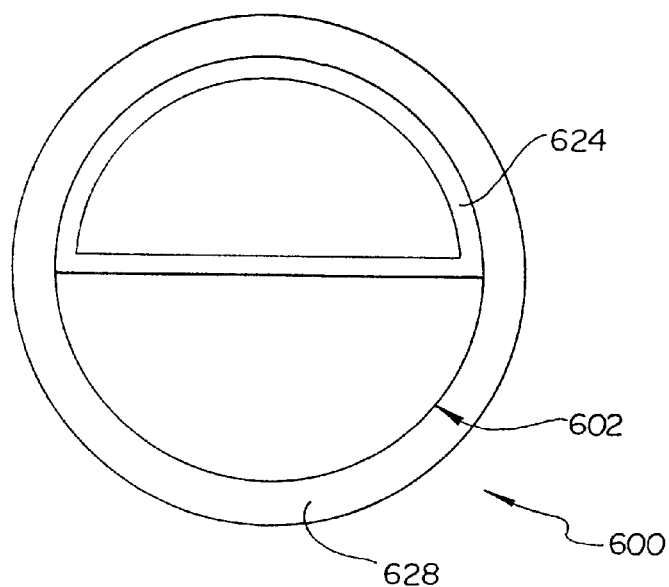
FIG. 21 is a transverse cross-sectional view of an additional exemplary embodiment of a catheter shaft including an elongate support member in accordance with the present invention.

FIG. 21 is a transverse cross-sectional view of an additional exemplary embodiment of catheter shaft 600 in accordance with the present invention. Catheter shaft 600 includes an elongate support member 602, an inflation conduit 624, and a sheath 628 disposed about elongate support member 602 and inflation conduit 624. In the embodiment of FIG. 21 elongate support member 602 and inflation conduit 624 each have a generally D-shaped cross section.

Figure 22:
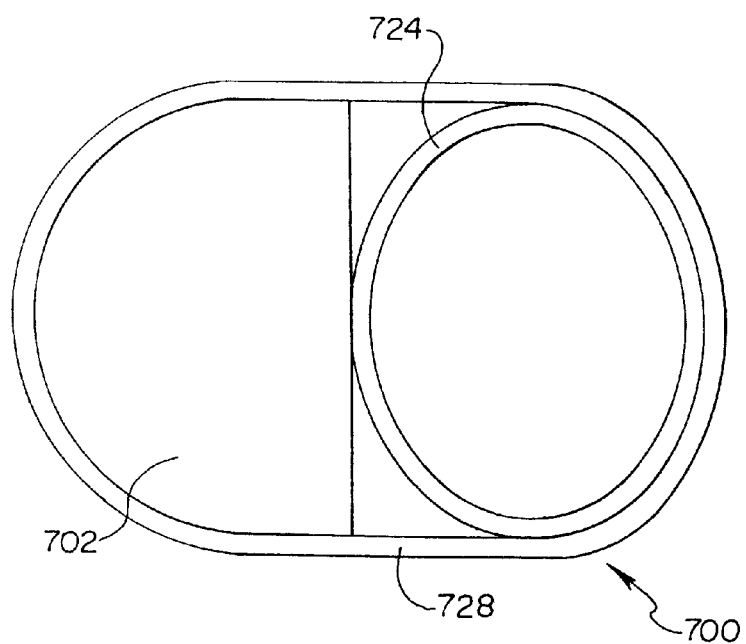
FIG. 22 is a transverse cross-sectional view of an additional exemplary embodiment of a catheter shaft including an elongate support member in accordance with the present invention.

FIG. 22 is a transverse cross-sectional view of an additional exemplary embodiment of catheter shaft 700 in accordance with the present invention. Catheter shaft 700 includes an elongate support member 702, an inflation conduit 724, and a sheath 728 disposed about elongate support member 702 and inflation conduit 724. In the embodiment of FIG. 22 elongate support member 702 has a generally D-shaped cross section, and inflation conduit 724 has a generally elliptical cross section.

Figure 23:
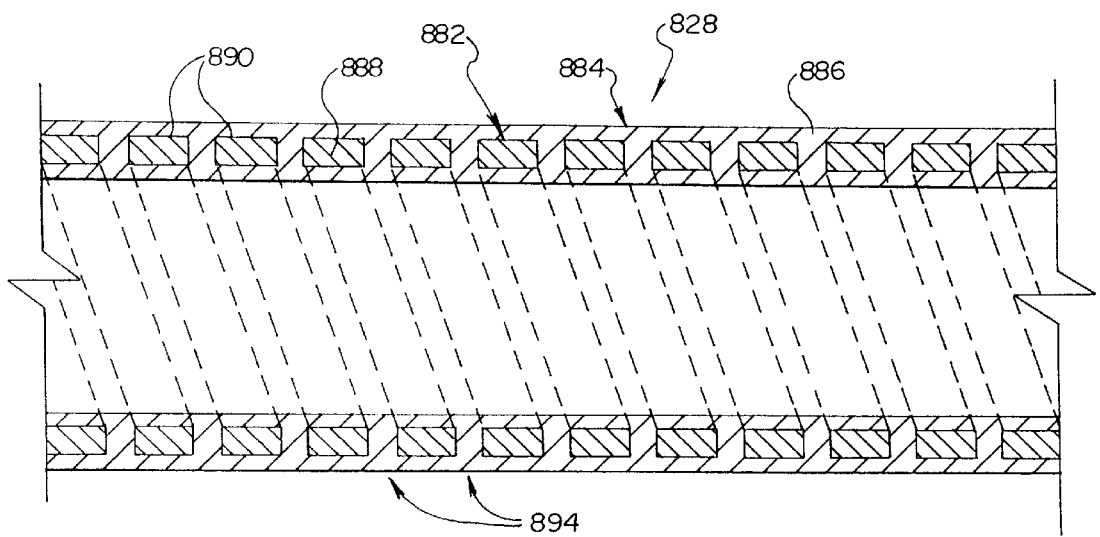
FIG. 23 is a longitudinal cross sectional view of an exemplary embodiment of a sheath in accordance with the present invention.

FIG. 23 is a longitudinal cross sectional view of an exemplary embodiment of a sheath 828 in accordance with the present invention. In the embodiment of FIG. 23, sheath 828 includes a support matrix 882 disposed within a jacket 884 comprising a jacket material 886. Support matrix 882 comprises a ribbon 888, preferably having a generally helical shape, forming a plurality of turns 890. Support matrix 882 also includes a plurality of gaps 894 defined by adjacent turns 890 of ribbon 888. As shown in FIG. 23, jacket material 886 of jacket 884 extends into gaps 894.

In a preferred embodiment, jacket material 886 comprises polyether block amide (PEBA). Polyether block amide is commercially available from Atochem Polymers of Birdsboro, Penn. under the trade name PEBAX. Jacket 884 may be fabricated using an extrusion process. In this process, molten PEBA may be extruded over support matrix 882 filling gaps 894. It is to be understood that other manufacturing processes may be used without departing from the spirit and scope of the present invention. Jacket 884 may also be comprised of other materials without departing from the spirit of scope of this invention. Examples of materials which may be suitable in some applications include: thermoplastics, high performance engineering resins, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), and the like. Also in a preferred embodiment, ribbon 888 comprises a metal. Particularly preferred metals include stainless steel, nickel-titanium alloy, nickel alloys, and titanium alloys.

Figure 24:
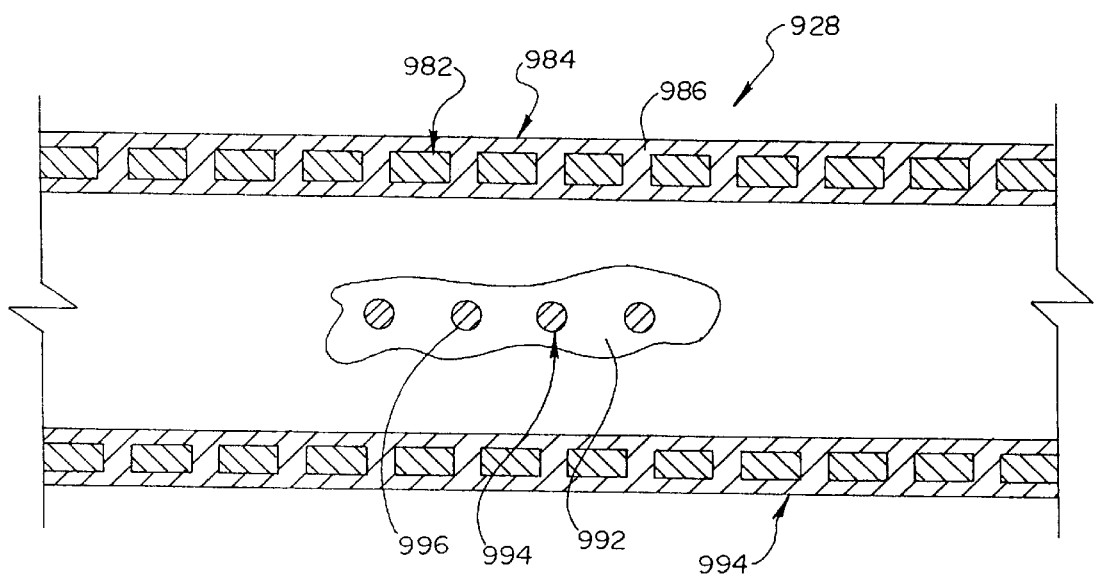
FIG. 24 is a longitudinal cross sectional view of an additional exemplary embodiment of a sheath in accordance with the present invention.

FIG. 24 is a longitudinal cross sectional view of an additional exemplary embodiment of a sheath 928 in accordance with the present invention. In the embodiment of FIG. 24, sheath 928 includes a support matrix 982 disposed within a jacket 984 comprising a jacket material 986. Support matrix 982 comprises a wall 992 defining a plurality of perforations 994. In the embodiment of FIG. 24, each perforation 994 comprises a generally circular hole 996. As shown in FIG. 24, jacket material 986 of jacket 984 extends into perforations 994 defined by wall 992 of support matrix 982. It is to be understood that perforations 994 may be any shape without deviating from the spirit and scope of the present invention. Jacket material 986 may comprise various materials without deviating from the spirit and scope of the present invention. Examples of materials which may be suitable in some applications include: thermoplastics, high performance engineering resins, polyethylene (PE), polypropylene (PP), polyvinylchloride (PVC), polyurethane, polytetrafluoroethylene (PTFE), polyetherether ketone (PEEK), polyimide, polyamide, polyphenylene sulfide (PPS), polyphenylene oxide (PPO), polysufone, nylon, perfluoro(propyl vinyl ether) (PFA), polyether block amide (PEBA), and the like.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A catheter shaft, comprising:
   a metallic elongate support member having an outer surface, a length, and a cross section perpendicular to the length; the cross section having a center of area defined by the outer surface, a first distance between the center of area and the outer surface, and a second distance between the center of area and the outer surface; wherein the first distance is different from the second distance; and
   a sheath disposed about the elongate support member.

2. The catheter shaft of claim 1, wherein the elongate support member comprises stainless steel.

3. The catheter shaft of claim 1, wherein the elongate support member comprises nickel alloy.

4. The catheter shaft of claim 1, wherein the elongate support member comprises nickel titanium alloy.

5. The catheter shaft of claim 1, wherein the sheath comprises polyether-ether ketone.

6. The catheter shaft of claim 1, wherein the sheath comprises polyimide.

7. The catheter shaft of claim 1, wherein the sheath comprises polyphenylene sulfide.

8. The catheter shaft of claim 1, wherein the sheath comprises perfluoro(propyl vinyl ether).

9. The catheter shaft of claim 1, wherein the center of gravity lies on the cross section.

10. The catheter shaft of claim 1, wherein the center of gravity lies off the cross section.

11. A support member for supporting a catheter shaft, comprising:
    a distal end, a proximal end, and a plurality of elongate flanges extending therebetween;
    each elongate flange having a fixed end and a free end; and
    the fixed end of each flange being fixed to a central portion of the elongate support member.

12. The support member of claim 11, wherein the plurality of elongate flanges define at least one elongate channel having an elongate opening.

13. The support member of claim 12, wherein the at least one elongate channel extends between the proximal end of the support member and the distal end of the support member.

14. The support member of claim 12, wherein the elongate opening of the at least one elongate channel extends between the proximal end of the support member and the distal end of the support member.

15. The support member of claim 12, wherein the elongate opening of the at least one elongate channel is disposed between the free ends of a plurality of the flanges.

16. The support member of claim 11, wherein the flanges are adapted to absorb bending energy during bending of the support member.

17. The support member of claim 11, wherein the flanges are adapted to deflect during bending of the support member.

18. The support member of claim 11, wherein the distal ends of the flanges are adapted to move relative to one another during bending of the elongate support member.

19. A catheter shaft, comprising:
    a support member including a distal end, a proximal end, and a plurality of elongate flanges extending therebetween;
    each elongate flange having a fixed end and a free end;
    the fixed end of each flange being fixed to a central portion of the elongate support member; and
    a sheath disposed about the support member.

20. The catheter shaft of claim 19, wherein the elongate flanges of the support member define at least one elongate channel.

21. The catheter shaft of claim 20, further including an inflation conduit at least partially disposed within the at least one elongate channel defined by the support member.

22. The catheter shaft of claim 21, wherein the inflation conduit defines an inflation lumen.

23. The support member of claim 20, wherein the at least one elongate channel extends between the proximal end of the support member and the distal end of the support member.

24. The support member of claim 20, wherein an elongate opening of the at least one elongate channel extends between the proximal end of the support member and the distal end of the support member.

25. The support member of claim 24, wherein the elongate opening of the at least one elongate channel is disposed between the free ends of a plurality of the flanges.

26. The support member of claim 24, wherein the flanges are adapted to absorb bending energy during bending of the support member.

27. The support member of claim 19, wherein the flanges are adapted to deflect during bending of the support member.

28. The support member of claim 19, wherein the distal ends of the flanges are adapted to move relative to one another during bending of the elongate support member.

29. The support member of claim 19, further including:

a right portion comprising one or more flanges extending beyond a right side of a first central plane extending through a longitudinal axis of the elongate support member;

a left portion comprising one or more flanges extending beyond a left side of the first central plane;

a ventral portion comprising one or more flanges extending beyond a ventral side of a second central plane extending through the longitudinal axis of the elongate support member; and a dorsal portion comprising one or more flanges extending beyond a dorsal side of the second central plane.

30. The support member of claim 29, wherein the ventral portion has a transverse cross sectional area which is substantially equal to a transverse cross sectional area of the dorsal portion.

31. The support member of claim 29, wherein the right portion has a transverse cross sectional area which is substantially equal to a transverse cross sectional area of the left portion.

32. The support member of claim 29, wherein a transverse cross sectional area the ventral portion, a transverse cross sectional area the dorsal portion, a transverse cross sectional area the right portion, and a transverse cross sectional area the left portion are all substantially equal.

33. The support member of claim 29, wherein the support member is resistant to bending along the first central plane.

34. The support member of claim 29, wherein the support member is resistant to bending along the second central plane.

35. The support member of claim 29, wherein the support member is resistant to bending along the first central plane and the second central plane.

36. The support member of claim 35, wherein the resistance of the support member to bending along the first central plane is substantially equal to the resistance of the support member to bending along the second central plane.

37. The support member of claim 29, wherein the longitudinal axis extends through a center of gravity of the support member.

38. The support member of claim 29, wherein the second central plane is disposed at an angle to the first central plane.

39. The support member of claim 29, wherein the second central plane is disposed at about a right angle to the first central plane.

40. The support member of claim 29, wherein the support member is symmetrical about the first central plane.

41. The support member of claim 29, wherein the support member is asymmetrical about the second central plane.

42. The support member of claim 29, wherein the first central plane comprises a neutral plane when the support member is bent along the second central plane.

43. The support member of claim 29, wherein the second central plane comprises a neutral plane when the support member is bent along the first central plane.

44. A catheter shaft, comprising:

a ribbon forming a plurality of turns;

a plurality of gaps defined by adjacent turns of the ribbon; and a jacket comprising a jacket material surrounding at least a portion of the ribbon and extending into the gaps.

45. The catheter shaft of claim 44, wherein the turns formed by ribbon comprise a helix.

46. The catheter shaft of claim 44, wherein the ribbon comprises stainless steel.

47. The catheter shaft of claim 44, wherein the ribbon comprises nickel alloy.

48. The catheter shaft of claim 46, wherein the ribbon comprises nickel titanium alloy.

49. The catheter shaft of claim 46, wherein the jacket material comprises polyether-ether ketone.

50. The catheter shaft of claim 46, wherein the jacket material comprises polyimide.

51. The catheter shaft of claim 46, wherein the jacket material comprises polyphenylene sulfide.

52. The catheter shaft of claim 46, wherein the jacket material comprises perfluoro(propyl vinyl ether).

53. A catheter shaft, comprising:

a wall defining a plurality of perforations; and a jacket formed of a jacket material overlaying the wall and extending into the perforations.

54. The catheter shaft of claim 53, wherein the perforations have a cylindrical shape.

55. The catheter shaft of claim 53, wherein the wall comprises stainless steel.

56. The catheter shaft of claim 53, wherein the wall comprises a nickel alloy.

57. The catheter shaft of claim 53, wherein the wall comprises a nickel titanium alloy.

58. The catheter shaft of claim 53, wherein the jacket material comprises polyether-ether ketone.

59. The catheter shaft of claim 53, wherein the jacket material comprises polyimide.

60. The catheter shaft of claim 53, wherein the jacket material comprises polyphenylene sulfide.

61. The catheter shaft of claim 53, wherein the jacket material comprises perfluoro(propyl vinyl ether).

* * * * *